United States Patent
Huang et al.

(10) Patent No.: US 11,759,124 B2
(45) Date of Patent: Sep. 19, 2023

(54) REAL-TIME DYNAMIC AND QUANTITATIVE DETECTION DEVICE FOR CARBON DIOXIDE IN HUMAN EXHALED AIR

(71) Applicant: SHANGHAI UNIVERSITY OF MEDICINE & HEALTH SCIENCES, Shanghai (CN)

(72) Inventors: Gang Huang, Shanghai (CN); Lijun Hao, Shanghai (CN); Jun Zhu, Shanghai (CN)

(73) Assignee: SHANGHAI UNIVERSITY OF MEDICINE & HEALTH SCIENCES, Shanghai (CN)

( * ) Notice: Subject to any disclaimer, the term of this patent is extended or adjusted under 35 U.S.C. 154(b) by 343 days.

(21) Appl. No.: 17/156,710

(22) Filed: Jan. 25, 2021

(65) Prior Publication Data
US 2021/0228106 A1 Jul. 29, 2021

(30) Foreign Application Priority Data
Jan. 23, 2020 (CN) .......................... 202010076637.4

(51) Int. Cl.
*A61B 5/083* (2006.01)
*G01N 33/497* (2006.01)

(52) U.S. Cl.
CPC .......... *A61B 5/0836* (2013.01); *G01N 33/497* (2013.01)

(58) Field of Classification Search
CPC .......... A61M 2230/432; A61M 16/085; A61M 2016/0413; A61M 2230/202;
(Continued)

(56) References Cited

U.S. PATENT DOCUMENTS

2004/0017570 A1* 1/2004 Parikh ................ G01N 21/6428
356/437
2005/0085740 A1* 4/2005 Davis ................... G01N 33/497
422/84
(Continued)

*Primary Examiner* — Eric J Messersmith
(74) *Attorney, Agent, or Firm* — HAMRE, SCHUMANN, MUELLER & LARSON, P.C.

(57) ABSTRACT

Disclosed is a real-time dynamic and quantitative detection device for carbon dioxide in human exhaled air, which comprises: a face mask which comprises an air inlet and an air outlet; an inhalation channel connected with the air inlet of the face mask, a first one-way valve is provided in the inhalation channel; an exhalation channel connected with the air outlet of the face mask, a second one-way valve is provided in the exhalation channel; an air path switching element connected with the exhalation channel to realize the switching between an exhalation air path to be detected and an inflation air path; a detection air chamber connected with the exhalation channel, at least one carbon dioxide sensor connected with an external upper computer is provided in the detection air chamber; before detection, the air path switching element switches to the inflation air path to clean and initialize the detection air chamber; during detection, the air path switching element switches to the exhalation air path to be detected, then the human exhaled air enters the detection air chamber through the exhalation channel, and real-time dynamic and quantitative detection of carbon dioxide in the exhaled air is realized by the carbon dioxide sensor. Compared with the prior art, the present invention has the advantages of high detection precision, convenient use, and the like.

11 Claims, 2 Drawing Sheets

(58) Field of Classification Search
CPC ........... A61M 2202/0225; A61B 5/082; A61B 5/0836; A61B 5/083
See application file for complete search history.

(56) References Cited

U.S. PATENT DOCUMENTS

| | | | | |
|---|---|---|---|---|
| 2013/0259749 | A1* | 10/2013 | Moretti | A61B 5/742 |
| | | | | 436/133 |
| 2014/0128691 | A1* | 5/2014 | Olivier | G16H 20/60 |
| | | | | 600/323 |
| 2014/0235961 | A1* | 8/2014 | Brugnoli | G01N 19/10 |
| | | | | 600/301 |
| 2014/0326048 | A1* | 11/2014 | Jaffe | A61B 5/082 |
| | | | | 73/31.05 |
| 2015/0032019 | A1* | 1/2015 | Acker | A61B 5/097 |
| | | | | 600/532 |
| 2016/0327541 | A1* | 11/2016 | Reinstaedtler | A61B 5/0833 |
| 2017/0112413 | A1* | 4/2017 | Brugnoli | G01N 33/497 |
| 2019/0120821 | A1* | 4/2019 | Atsalakis | A61B 5/0803 |
| 2019/0231222 | A1* | 8/2019 | Ahmad | A61B 5/091 |
| 2021/0378546 | A1* | 12/2021 | Xian | A61B 5/083 |

* cited by examiner

REAL-TIME DYNAMIC AND QUANTITATIVE DETECTION DEVICE FOR CARBON DIOXIDE IN HUMAN EXHALED AIR

FIELD OF TECHNOLOGY

The invention belongs to the technical field of medical apparatus, and relates to a carbon dioxide detection device, in particular to a real-time dynamic and quantitative detection device for carbon dioxide in human exhaled air.

BACKGROUND

The human respiratory system is one of the eight major systems of human body. Respiration maintains normal human physiological activities and is also an important indicator of human health. Whether the respiratory system is diseased or other major internal organs are diseased, when these diseases deteriorate to a certain extent, they will affect the respiratory center. The failure of most internal organs often leads to the failure of respiratory function. The failure of respiratory function aggravates the failure of other internal organs and systems, forming a vicious circle.

The role of respiration is to exchange air with outside air, inhale oxygen and exhale carbon dioxide, so it can directly reflect the physiological condition of human body.

At present, the electronic measurement system for carbon dioxide air analysis mainly consists of infrared analyzer and mass spectrometer. Clinical infrared analyzers are generally used for anesthesia analysis of respiratory carbon dioxide; while mass spectrometers are generally considered to be the best means for respiratory air analysis because it has the characteristics of quick response, capability of measuring dry gas, measurement, accuracy stability, and the like. However, these systems have obvious shortcomings, such as high cost, large size and regular maintenance. In addition, these products need constant sampling, and the change of temperature and humidity will lead to delay of analysis results and slower response speed.

There are two types of instruments or modules for monitoring carbon dioxide: direct current type and bypass type. The former is more invasive, while the latter uses sampling for detection. These two methods are not convenient for long-term continuous monitoring, and the post-processing of carbon dioxide in the exhaled air is not considered, which may cause the carbon dioxide concentration in the human inhaled air to be too high.

SUMMARY

The objective of the present invention is to provide a real-time dynamic and quantitative detection device for carbon dioxide in human exhaled air to overcome the shortcomings in the prior art.

The objective of the present invention can be achieved through the following technical solutions:

A real-time dynamic and quantitative detection device for carbon dioxide in human exhaled air comprises:
- a face mask which comprises an air inlet and an air outlet;
- an inhalation channel connected with the air inlet of the face mask, a first one-way valve is provided in the inhalation channel;
- an exhalation channel connected with the air outlet of the face mask, a second one-way valve is provided in the exhalation channel;
- an air path switching element connected with the exhalation channel to realize the switching between an exhalation air path to be detected and an inflation air path;
- a detection air chamber connected with the exhalation channel, at least one carbon dioxide sensor connected with an external upper computer is provided in the detection air chamber;
- before detection, the air path switching element switches to the inflation air path to clean and initialize the detection air chamber; during detection, the air path switching element switches to the exhalation air path to be detected, then the human exhaled air enters the detection air chamber through the exhalation channel, and real-time dynamic and quantitative detection of carbon dioxide in the exhaled air is realized by the carbon dioxide sensor.

Further, the air path switching member is a three-way valve.

Further, a micropump connected with the external upper computer is provided in the detection air chamber.

Further, the device comprises a carbon dioxide absorber connected to an end of the detection air chamber.

Further, the air path switching element is connected with an automatic inflation component, and when the air path switching element switches to the inflation air path, the automatic inflation component is communicated with the inflation air path.

Further, the automatic inflation component comprises an air pump connected with the external upper computer.

Further, the inflation air source of the automatic inflation component is ambient air or oxygen.

Further, the carbon dioxide sensor is an NDIR infrared carbon dioxide sensor.

Further, the carbon dioxide sensor is placed flat on the side wall of the detection air chamber.

Further, the micropump is provided opposite to the carbon dioxide sensor.

Further, the face mask has an edge contour matching the contour of human face.

Further, after a set period of time, a total amount of exhaled carbon dioxide is detected by the carbon dioxide absorber.

Compared with the prior art, the present invention has the following beneficial effects:

1. According to the present invention, carbon dioxide in exhaled air is continuously and dynamically detected in real time with at least one highly sensitive carbon dioxide sensor placed in the detection air chamber, and carbon dioxide in exhaled air is absorbed and processed, thus overcoming the shortcomings existing in the prior art.
2. According to the present invention, by switching the air path, the automatic purging and initialization detection of the air path is achieved, thus realizing the convenience of testing and the relative independence of exhalation detection for different human bodies.
3. According to the present invention, the air inlet and the air outlet of the real-time dynamic and quantitative detection device for carbon dioxide in human exhaled air is provided with one-way valves, which can ensure the unidirectional inflow and outflow of air flow, separate the exhaled air, and all the exhaled air flows to the detection air chamber.
4. According to the present invention, a carbon dioxide absorber is further provided, and through the one-way valve, the air channel and the carbon dioxide absorber, a detection environment which is closed for carbon dioxide but the air flow can normally enter and exit is constructed, so that the dynamic detection of carbon dioxide in the human exhaled air can be realized without affecting the normal respiration of the human body; at the same time, the carbon dioxide absorber cuts off the mixture of carbon dioxide in exhaled air and ambient air, and constructs a relatively closed measuring air chamber, thus realizing the dynamic detection of carbon dioxide in exhaled air without affecting the normal respiration of human body, and reducing the environmental pollution at the same time.

5. Through the design of the detection device, the exhaled air enters the detection air chamber through the one-way valve and is discharged normally. With the change of the exhaled air, the carbon dioxide concentration is detected by a highly sensitive sensor, which is convenient for doctors through the change of the metabolite carbon dioxide.
6. A micropump is provided in the detection air chamber, which can rectify the exhaled air, keep relatively stable flow rate of the air flow to be detected, and avoid the air vortex from covering the sensor surface.
7. The present invention is convenient to use and operate. Before each detection, we need to clean the detection air chamber, purge the residual air from the previous measurement, and provide the measurement reference value. During detection, the dynamic change value of carbon dioxide in human exhaled air can be detected in real time by switching the air path to the exhalation channel.

DESCRIPTION OF THE EMBODIMENTS

The present invention will be described in detail with reference to the drawings and specific embodiments. The following embodiments are implemented based on the technical solution of the present invention, and a detailed embodiment and specific operation process are given, but the protection scope of the present invention is not limited to the following embodiments.

Figure 1:
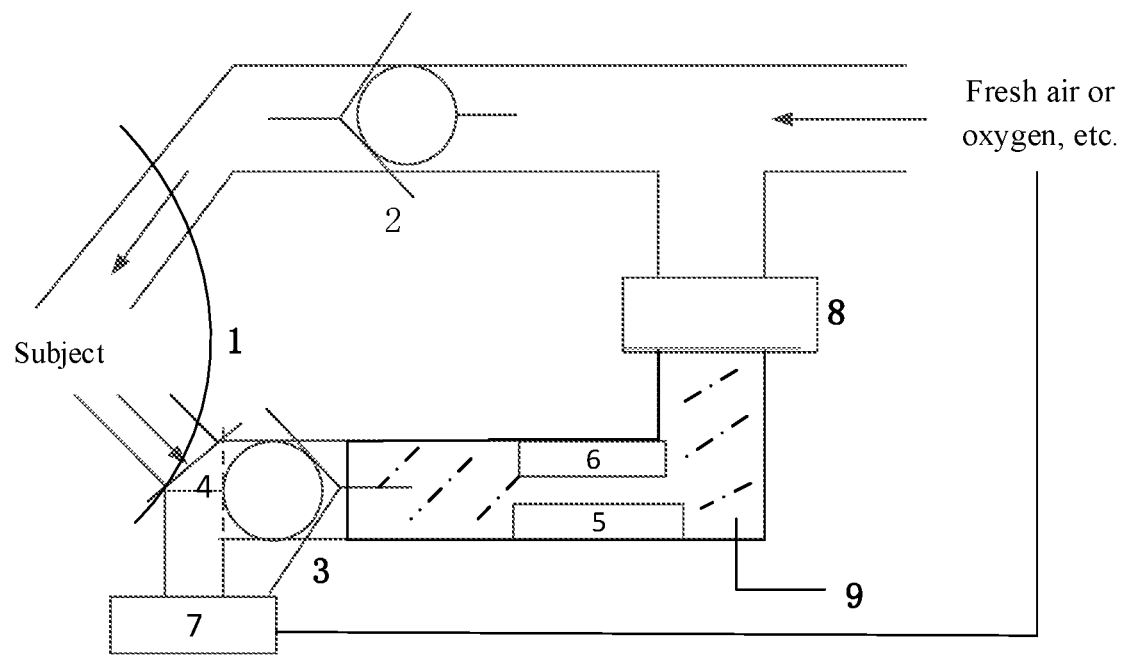
FIG. 1 is a structural diagram of the detection device of the present invention.
Figure 2:
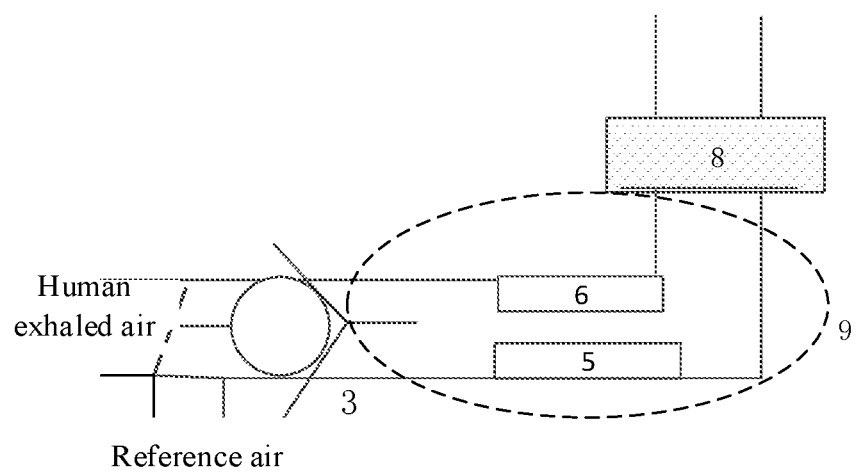
FIG. 2 is a schematic diagram of the exhalation process detection according to the present invention.

As shown in FIGS. 1-2, in an embodiment, a real-time dynamic and quantitative detection device for carbon dioxide in human exhaled air is provided, which comprises a face mask 1, an inhalation channel, an exhalation channel, an air path switching element 4 and a detection air chamber 9, wherein the face mask 1 comprises an air inlet and an air outlet, and can be worn on a human face, and is used for collecting air exhaled by human body through the mouth and nostrils and realizing inhalation; the inhalation channel is connected with the air inlet of the face mask 1, and a first one-way valve 2 is provided in the inhalation channel; the exhalation channel is connected with the air outlet of the face mask 1, and a second one-way valve 3 is provided in the exhalation channel; the air path switching element 4 is connected with the exhalation channel, and realizes the switching between the exhalation air path to be detected and the inflation air path according to different detection stages; the detection air chamber 9 is connected with the exhalation channel, and at least one carbon dioxide sensor 5 connected with an external upper computer is provided in the detection air chamber 9, constructing a dynamic testing environment of carbon dioxide to measure the instantaneous value of carbon dioxide in exhaled air over time.

The first one-way valve 2 in the inhalation channel controls the airflow direction of the air inlet, and fresh air or oxygen with different concentrations is inhaled into the human body through the first one-way valve, and exhaled air is prevented from flowing out of the air inlet at the same time. The second one-way valve 3 in the exhalation channel controls the air flow direction of the air outlet, and the exhaled air enters the detection air chamber through the second one-way valve, and exhaled air is prevented from returning to the human body at the same time.

In another embodiment, a flowmeter 10 may be provided in the exhalation channel.

Figure 3:
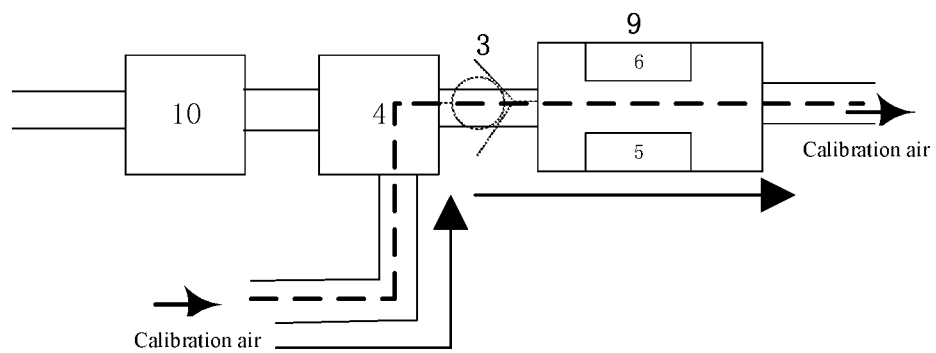
FIG. 3 is a schematic diagram of the air path switching element of the present invention after switching to the inflation air path.
Figure 4:
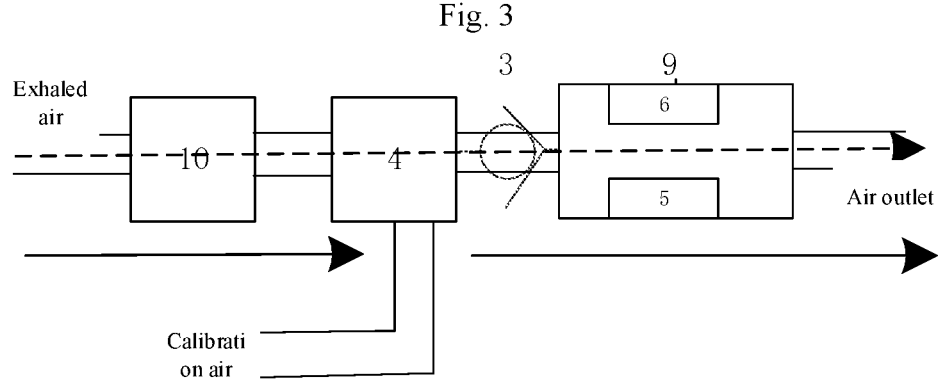
FIG. 4 is a schematic diagram of the air path switching element of the present invention after switching to the exhaled air path to be detected.

As shown in FIG. 3, before each detection, the air path switching element 4 switches to the inflation air path to clean and initialize the detection air chamber 9, and at the same time, the measurement reference value is obtained by using the relatively stable air in the closed air chamber. There are three objectives of inflation: the first is to purge the air chamber to eliminate the influence of residual air, and keep the pressure and temperature in the air chamber constant during each measurement to construct a stable measurement environment; the second is to preheat the sensor, so that the working performance of the sensor is stable and the sensor responds in time; the third is to obtain the measured reference value, and eliminate the environmental impact. During detection, the air path switching element 4 switches to the exhaled breath path to be detected, and the human exhaled air enters the detection air chamber 9 through the exhalation channel, and real-time dynamic and quantitative detection of carbon dioxide in the exhaled air is realized by the carbon dioxide sensor 5, as shown in FIG. 4. In this embodiment, the air path switching element 4 is a three-way valve.

In another embodiment, a micropump 6 connected with the external upper computer is further provided in the detection air chamber 9, which can rectify exhaled air through the micropump, keep relatively stable flow rate of the air flow to be measured, avoid the air vortex from covering the sensor surface, and solve the problem of inaccurate measurement results caused by unstable air flow and excessive dilution of air concentration. The size of the micropump 6 is determined according to the size of the detection air chamber, and the size can be as small as possible on the principle of not blocking the air flow. In the detection chamber 9, the micropump 6 may be placed opposite to the carbon dioxide sensor 5.

In this embodiment, the detection device also includes a carbon dioxide absorber 8 connected to the end of the detection chamber 9, the carbon dioxide absorber 8 is used for absorbing carbon dioxide in the air flowing out of the detection chamber and preventing carbon dioxide in the air from entering the detection chamber. Due to the arrangement of the carbon dioxide absorber 8, the detection air chamber is open for exhaled air, and the exhaled air can be discharged normally; but for carbon dioxide in exhaled air, the detection chamber is closed. The carbon dioxide absorber 8 can absorb and process carbon dioxide in exhaled air and ambient air, and block carbon dioxide in exhaled air and ambient air from entering the detection chamber.

The carbon dioxide absorber 8 includes a breathable shell and a carbon dioxide absorbent provided in the breathable shell, and a filtering membrane is installed on the breathable shell to prevent the carbon dioxide absorbent from being scattered. In this embodiment, calcium hydroxide is used as the carbon dioxide absorbent. The air outlet of the carbon dioxide absorber 8 is provided with an indicator or an alarm to remind for timely replacement of the carbon dioxide absorber.

The carbon dioxide absorber 8 can stably absorb carbon dioxide in exhaled air and detect the accumulated carbon dioxide, which can not only effectively prevent carbon dioxide in the air from re-entering the detection chamber, but also evaluate the total amount of carbon dioxide exhaled.

The air path switching element 4 is connected with an automatic inflation module 7, and when the air path switching element 4 switches to the inflation air path, the automatic inflation module 7 is communicated with the inflation air path. In this embodiment, the automatic inflation component 7 includes an air pump connected with the external upper computer. The inflation air source (calibration air or reference air) of the automatic inflation module 7 is ambient air (fresh air) or oxygen.

In this embodiment, the carbon dioxide sensor 5 is an NDIR infrared carbon dioxide sensor. The exhaled air in the detection air chamber changes dynamically, and the instantaneous value of carbon dioxide concentration in the exhaled air over time can be measured in real time by using a highly sensitive and highly responsive sensor. The detection performance of the sensor is affected by ambient temperature, humidity, and pressure. The carbon dioxide sensor is placed flat on the side wall of the detection air chamber pipeline, so as to avoid the exhalation vortex from covering the sensor surface and failing to respond in time.

In this embodiment, the edge contour of the face mask 1 matches the contour of human face.

The air pipeline of the detection device is made of materials with stable chemical properties and no air adsorption, such as aluminum alloy materials. The width of the air path pipeline should not be too narrow, so as to avoid too much air path resistance, which will affect the normal exhalation; when the width is determined, the appropriate length may be selected.

Figure 5:
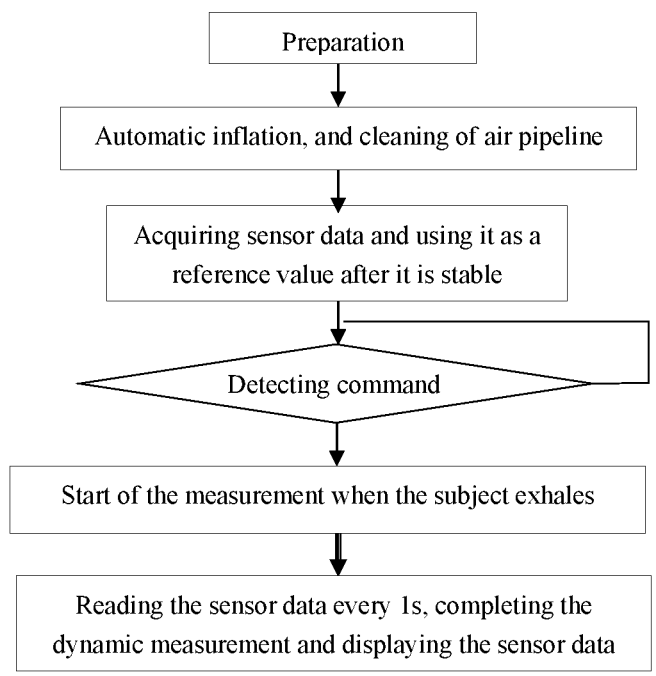
FIG. 5 is a flow chart for use of the present invention.
Drawings: 1—Face mask, 2—First one-way valve, 3—Second one-way valve, 4—Air path switching element, 5—Carbon dioxide sensor, 6—Micropump, 7—Automatic inflation component, 8—Carbon dioxide absorber, 9—Detection air chamber, 10—Flowmeter.

As shown in FIG. 5, the working process of the above-mentioned real-time dynamic and quantitative detection device for carbon dioxide in human exhaled air is as follows:

Before each measurement, there is a period for preparation, during which the cleaning of the measuring air chamber and the acquisition of the measurement reference value are completed. After the stable reference value is measured, the inflation is kept at a certain speed until the human exhalation is measured. After receiving the exhalation measurement command, the air path is switched to the exhalation channel, and the concentration value of carbon dioxide in the exhalation is detected in real time.

A specific application of the detection device is as follows: since *Helicobacter pylori* (HP) contains urease, which can decompose urea into carbon dioxide, if urea breath test is used to check *Helicobacter pylori* infection, urea substrate is first introduced into the body, and when HP in the stomach encounters urea, the urea will be decomposed into carbon dioxide. Carbon dioxide is absorbed through the gastrointestinal tract, reaches the lungs through the blood circulation, and is then discharged by exhalation. However, normal people do not have *Helicobacter pylori*, and urea is not decomposed, thus the urea is discharged through urinary system. By comparing and detecting the carbon dioxide changes in the human exhaled air before and after swallowing the urea substrate, the presence or absence of *Helicobacter pylori* infection can be accurately judged. We can dynamically know the conversion of urea by using the device to detect the concentration of carbon dioxide in human exhaled air in real time, and then know the presence or absence of *Helicobacter pylori* in the human body.

The preferred embodiments of the present invention have been described in detail above. It should be understood that those skilled in the art can make many modifications and changes according to the idea of the present invention without creative work. Therefore, all technical solutions that can be obtained by those skilled in the art through logical analysis, reasoning, or limited experiments on the basis of the prior art according to the idea of the present invention shall fall within the protection scope of the present invention.

What is claimed is:

1. A real-time dynamic and quantitative detection device for carbon dioxide in human exhaled air, comprising:
   a face mask, comprising an air inlet and an air outlet;
   an inhalation channel connected with the air inlet of the face mask, wherein a first one-way valve is provided in the inhalation channel;
   an exhalation channel connected with the air outlet of the face mask, wherein a second one-way valve is provided in the exhalation channel;
   an air path switching element connected with the exhalation channel to realize switching between an exhalation air path to be detected and an inflation air path;
   a detection air chamber connected with the exhalation channel, wherein at least one carbon dioxide sensor connected with an external upper computer is provided in the detection air chamber; and
   a carbon dioxide absorber is connected to an end of the detection air chamber, wherein:
   the carbon dioxide absorber comprises a first side opposite to a second side,
   the first side is connected to the end of the detection air chamber,
   the second side is connected to the inhalation channel, and
   the carbon dioxide absorber is configured to prevent carbon dioxide re-entering the detection air chamber,
   wherein, the real-time dynamic and quantitative detection device is configured such that, before detection, the air path switching element switches to the inflation air path to clean and initialize the detection air chamber; during detection, the air path switching element switches to the exhalation air path to be detected, then the human exhaled air enters the detection air chamber through the exhalation channel, and real-time dynamic and quantitative detection of carbon dioxide in the human exhaled air is realized by the at least one carbon dioxide sensor.

2. The real-time dynamic and quantitative detection device for carbon dioxide in human exhaled air according to claim 1, wherein the air path switching element is a three-way valve.

3. The real-time dynamic and quantitative detection device for carbon dioxide in human exhaled air according to claim 1, wherein a micropump connected with the external upper computer is further provided in the detection air chamber.

4. The real-time dynamic and quantitative detection device for carbon dioxide in human exhaled air according to claim 1, wherein the air path switching element is connected with an automatic inflation component, and when the air path switching element switches to the inflation air path, the automatic inflation component is communicated with the inflation air path.

5. The real-time dynamic and quantitative detection device for carbon dioxide in human exhaled air according to claim 4, wherein the automatic inflation component comprises an air pump connected with the external upper computer.

6. The real-time dynamic and quantitative detection device for carbon dioxide in human exhaled air according to claim 4, wherein an inflation air source of the automatic inflation component is ambient air or oxygen.

7. The real-time dynamic and quantitative detection device for carbon dioxide in human exhaled air according to claim 1, wherein the at least one of carbon dioxide sensor is an NDIR infrared carbon dioxide sensor.

8. The real-time dynamic and quantitative detection device for carbon dioxide in human exhaled air according to claim 1, wherein the face mask has an edge contour matching a contour of human face.

9. The real-time dynamic and quantitative detection device for carbon dioxide in human exhaled air according to claim 1, wherein after a set period of time, a total amount of exhaled carbon dioxide is detected by the carbon dioxide absorber.

10. The real-time dynamic and quantitative detection device for carbon dioxide in human exhaled air of claim 1, wherein the carbon dioxide absorber is disposed in a breathable shell having a filtering membrane configured to prevent scattering of the carbon dioxide absorber.

11. The real-time dynamic and quantitative detection device for carbon dioxide in human exhaled air of claim 1, wherein the carbon dioxide absorber is configured such that, for carbon dioxide in the human exhaled air, the detection air chamber is closed.

* * * * *